United States Patent [19]
Dobbs et al.

[11] Patent Number: 5,912,938
[45] Date of Patent: Jun. 15, 1999

[54] TOMOGRAPHY SYSTEM HAVING DETECTORS OPTIMIZED FOR PARALLEL BEAM IMAGE RECONSTRUCTION

[75] Inventors: John Dobbs, Hamilton; Ruvin Deych, Burlington, both of Mass.

[73] Assignee: Analogic Corporation, Peabody, Mass.

[21] Appl. No.: 08/726,638

[22] Filed: Oct. 7, 1996

[51] Int. Cl.⁶ .................................................. G01N 23/00
[52] U.S. Cl. .................................................. 378/19; 378/4
[58] Field of Search ........................................ 378/19, 4

[56] References Cited

U.S. PATENT DOCUMENTS

| | | | |
|---|---|---|---|
| 4,298,799 | 11/1981 | Oliver | 378/19 |
| 4,338,521 | 7/1982 | Shaw et al. | 250/366 |
| 4,365,339 | 12/1982 | Pavkovich et al. | 378/15 |
| 5,025,462 | 6/1991 | Saito et al. | 378/19 |
| 5,164,973 | 11/1992 | Takahashi et al. | 378/19 |
| 5,463,224 | 10/1995 | Burstein et al. | 250/366 |
| 5,487,098 | 1/1996 | Dobbs et al. | 378/19 |

FOREIGN PATENT DOCUMENTS

| | | |
|---|---|---|
| 0 133 488 A1 | 7/1984 | European Pat. Off. . |
| 0 177 417 A1 | 9/1985 | European Pat. Off. . |
| 0 475 563 A1 | 5/1991 | European Pat. Off. . |

*Primary Examiner*—Craig E. Church
*Attorney, Agent, or Firm*—Lappin & Kusmer LLP

[57] ABSTRACT

An x-ray scanning system including an x-ray source defining a focal spot from which radiation is emitted, an x-ray detector assembly including a plurality of x-ray detectors cooperative with the x-ray source to define a radiation beam extending from the focal spot to all of the detectors, a support for supporting at least one of the x-ray source and the detector assembly for rotation about an isocenter, and means for configuring the detectors so that the increment in radial distance from the isocenter to the centers of any two adjacent sub-beams is a substantially constant value.

15 Claims, 9 Drawing Sheets

TOMOGRAPHY SYSTEM HAVING DETECTORS OPTIMIZED FOR PARALLEL BEAM IMAGE RECONSTRUCTION

TECHNICAL FIELD

This invention relates generally to x-ray computed tomography (CT) systems, and more particularly to arrangements for x-ray detectors within such systems.

BACKGROUND OF THE INVENTION

Third-generation CT scanners typically include an x-ray source and an array of x-ray detectors secured respectively on diametrically opposite sides of an annular disk, the latter being rotatably mounted within a gantry support. During a scan of a patient located within the opening of the disk, the disk rotates about a rotation axis while x-rays pass from the focal spot of the X-ray source through the patient to the detector system.

The x-ray source and detector array are positioned so that the x-ray paths between the focal spot and each detector all lie in the same plane (the so-called "slice plane", "rotation plane" or "scan plane") which is normal to the rotation axis of the disk. Because the ray paths originate from substantially a point source and extend at different angles to the detectors, the ray paths resemble a fan, and thus the term "fan beam" is used to describe all of the ray paths at any one instant of time. The term "sub-beam", as used herein, refers to the radiation that is detected by a single detector at a measuring instant during a scan. The sub-beam is partially attenuated by the mass of the patient in its path, and each detector generates a single intensity measurement as a function of the attenuation, and thus of the density of the portion of the patient in the path of the sub-beam from the focal spot to that detector. These x-ray intensity measurements, or projections, are typically performed during prescribed measurement intervals at each of a plurality of angular disk positions.

The term "radial", as used herein, refers to a direction in the scan plane from or toward the focal spot of the x-ray source. The term "tangential", as used herein, refers to a direction in the scan plane which is substantially perpendicular to the radial direction.

Various types of detectors have been developed, including gas and solid state types. A typical solid state detector includes a scintillating crystal which converts high energy x-radiation photons into low energy visible light photons, and a photodiode which converts the low energy visible light photons into extremely low-amplitude electrical currents (i.e., on the order of picoamperes to nanoamperes). The output of each detector represents the x-ray flux incident on the detector. The outputs of the detector array are transmitted via an array of conductors to a data acquisition system (DAS) for signal processing.

A typical gas detector comprises a pressure vessel with a radiation-translucent, or radiolucent, window which permits x-rays to enter the vessel with a minimum of attenuation. Within the vessel are a large number of electrically conductive plates of non-uniform dimension or nonuniform inter-plate spacings which are surrounded by a high-pressure inert gas, such as xenon, which is ionized by the x-rays. The conductive plates define discrete regions which are swept by electric fields. A region which supplies electrical charge to a particular plate defines a single sub-beam of radiation. The conductive plates can be radially oriented with respect to the axis of rotation of the scanner, thereby providing electric fields in the tangential direction. Alternatively, the plates can be oriented perpendicular to the rotation axis to provide electric fields in the axial direction.

The width in the tangential direction of a single detector (hereinafter, "detector" or "detector crystal") defines the width of a single sub-beam of radiation emitted from the x-ray source. Because resolution of the resulting image is a function of the width and spacing of the detectors, a CT scanner system typically includes hundreds of relatively small detectors which are extremely closely spaced along an arc of a circle extending about the focal spot. For example, one third-generation CT scanner system manufactured by the present assignee includes 384 detectors provided by 24 modules of 16 detectors each and closely spaced within a 48-degree arc extending about the focal spot. The width of a single detector in such prior art systems is thus on the order of a millimeter.

In so-called fan beam tomography, radiation is emitted in a fan-shaped beam from the x-ray source, and data about the object being scanned is obtained from a series of fan-shaped projections, or views, taken at constant angular increments about the patient. However, the complexity of the computations required to reconstruct images from the data can be significantly reduced if the fan beam data is grouped in sets of parallel beam data and the image reconstructed using parallel beam algorithms. To accomplish this, data from parallel rays from different projections are grouped together into sets. The parallel beam data sets are then interpolated so that the distance between adjacent sub-beams is a constant value. More specifically, interpolation of the parallel beam data sets ensures that the distance from the isocenter to successive adjacent sub-beams is a constant increment of the radius of the circle on which the detectors are located. This constant spacing between adjacent sub-beams is required for accurate image reconstruction using parallel beam convolution and back-projection methods.

A disadvantage of this technique is that interpolation of data is difficult and time-consuming, and the data obtained thereby is inherently of lower spatial resolution. It is therefore preferable to sample and obtain data substantially as it will be used in the reconstruction of an image, instead of obtaining data which must be significantly interpolated in order to approximate the information required to reconstruct images.

In prior art CT systems, the detectors have typically been spaced at equal angular increments along a circle centered at the focal spot. However, this detector configuration is not necessarily the most desirable configuration, as the radial extent of the detectors in this configuration may be relatively great, leaving little room for the patient and for other necessary components, including power sources and cables. Although the entire system could be made larger to accommodate such a detector configuration, it is preferred to make the system more compact and thus more convenient and cost-effective for the user.

It would therefore be advantageous to provide an x-ray scanning system which overcomes the limitations of the prior art systems.

OBJECTS OF THE INVENTION

It is therefore an object of the present invention to provide a CT scanner system in which the detectors are configured to provide data from which image reconstruction is accurately and relatively easily performed.

Another object of the present invention is to provide a CT scanner system in which interpolation of image data to obtain accurate reconstructed images is minimized to relatively minor corrections.

And still another object of the present invention is to provide a CT scanner system in which the relative area occupied by the detector assembly is reduced, and the relative area available to accommodate the patient is increased, as compared to corresponding areas in prior art CT scanner systems.

And yet another object of the present invention is to provide a CT scanner system in which the detectors need not be positioned at equal angular increments about the focal spot.

SUMMARY OF THE INVENTION

We have determined that the detectors of an x-ray scanning system need not be spaced at equal angular increments along a circle centered at the focal spot, as previously assumed in prior art systems. Indeed, it is desirable to have the detectors arranged so as to define x-ray sub-beams which are substantially uniformly spaced from one another with respect to the isocenter of the system. Such a detector configuration significantly reduces the complexity of the computations required for image reconstruction from the data obtained in a series of fan-beam projections and thus significantly reduces computation time and expense.

According to the invention, there is provided an x-ray scanning system of the type including (a) an x-ray source for defining a focal spot from which a beam of radiation is emitted, (b) an x-ray detector assembly including a plurality of x-ray detectors arranged in an array and cooperative with the x-ray source so as to define the beam of radiation from the focal spot to all of the detectors, and (c) means for supporting at least one of the x-ray source and the detector assembly for rotation in a rotation plane about a rotation axis so as to define an isocenter. The radiation beam is made up of a plurality of sub-beams, each sub-beam being defined as that portion of the radiation beam impinging on a single detector. The x-ray scanning system of the invention further comprises means for configuring the detectors so that the increment in radial distance from the isocenter to the centers of any two adjacent sub-beams is a substantially constant value.

According to one embodiment, the means for configuring the detectors comprises means for locating the detectors substantially on a circle centered at a point other than the focal spot. In this embodiment, the detectors are grouped in substantially linear arrays, and the centers of the arrays are located approximately on an arc of the detector circle within the scan plane. The detector circle is selected from a family of circles having a circumference which passes through the focal spot and being centered at a point on a line which extends from the focal spot and passes through the isocenter.

The x-ray scanning system can further include an anti-scatter plate assembly which includes a plurality of anti-scatter plates disposed between the x-ray source and the detector assembly. The anti-scatter plate assembly is mounted relative to the detector assembly so that the anti-scatter plates are substantially aligned with radial lines extending from the focal spot. The radiation detected by the detector assembly is thus substantially limited to radiation emitted directly from the x-ray source.

In a preferred embodiment, the anti-scatter plates are substantially aligned with regions of substantially constant maximum sensitivity of corresponding detectors. The number of anti-scatter plates can be equal to, greater than, or fewer than the number of detectors.

In the detector configuration of this embodiment of the invention, the detector arrays are positioned so that the increment in radial distance from the isocenter to proximate sub-beams defined by corresponding proximate detectors in adjacent arrays is approximately equal to the increment in radial distance from the isocenter to adjacent sub-beams defined by corresponding adjacent detectors in a single array.

Adjacent detectors in an array are spaced apart from one another by a region of relatively low sensitivity to radiation. The detector arrays are oriented at a preselected angle $\alpha$ with respect to a nominally perpendicular orientation of the arrays relative to radial lines extending from the focal spot to approximately the centers of the arrays. The regions of relatively low sensitivity to radiation between adjacent detectors in an array are thus not aligned with the radial lines but are instead tilted at an angle $\alpha$ with respect to the radial lines.

Each of the detectors includes a detector crystal for sensing the radiation. The absolute value of the angle $\alpha$ is a function of the height (in the radial direction) of the detector crystal and the width (in the tangential direction) of the regions of relatively low sensitivity to radiation between adjacent crystals in an array. The angle $\alpha$ includes both positive and negative values for the angle.

According to another aspect of the invention, the means for configuring the detectors comprises means for defining a plurality of sub-beams which subtend a plurality of different angles. According to this embodiment, a plurality of detectors having a corresponding plurality of different widths in the tangential direction is provided, with means for defining a locus of the detectors with respect to the focal spot. The width of a given detector, which defines the tangential extent of a sub-beam, is a function of the location of that detector with respect to a central ray extending from the focal spot and passing through the isocenter.

In one embodiment, the detectors are located at a constant distance from the focal spot, i.e., on a circle centered at the focal spot. In another embodiment, the detectors are located on a substantially straight line at a preselected distance from the focal spot.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which.

DETAILED DESCRIPTION OF THE DRAWINGS

An x-ray scanning system according to the present invention departs from the traditional detector configuration in which numerous detectors of substantially uniform width are equidistant from the focal spot and equiangularly spaced along an arc of a circle centered at the focal spot. This prior art detector configuration defines equiangularly spaced beams which are not uniformly spaced from one another relative to the isocenter of the scanner.

As previously discussed, for tomography systems which use parallel beam image reconstruction algorithms, uniform sub-beam spacing relative to the isocenter of the scanner system is desirable in order to avoid the introduction of artifacts resulting from the combined effects of insufficient data sampling and significant interpolation of such data. In the system of the present invention, approximately uniform or constant sub-beam spacing relative to the isocenter is achieved by relocating the detectors and, in some cases, varying their widths in the tangential dimension. The detector configurations of the present invention provide data which is essentially in the form required for accurate parallel beam image reconstruction, without the need for significant data interpolation.

One way to accomplish this objective, while maintaining the uniformity of the detector width dimension, is to locate detectors of uniform width on a circle centered at a point other than the focal spot. In particular, a circle which has a circumference that passes through the focal spot and which is centered at a point on a line extending from the focal spot and passing through the isocenter of the system provides data which can be used to simulate substantially uniformly spaced sub-beams relative to the isocenter. A family of circles can be identified which satisfy these criteria, as will be more fully detailed below.

Another way to accomplish this objective is to vary the detector width dimensions as a function of the location of a given detector relative to a so-called central ray defined by a line extending from the focal spot and passing through the isocenter. In this configuration the detectors can be located, for example, on a straight line at a preselected distance from the focal spot, or on some other locus.

According to the invention, the location and width of a given detector relative to the focal spot is selected so that the increment in radial distance from the isocenter to the centers of adjacent sub-beams, as defined by adjacent detectors, is a constant value. As explained more fully below, the distance $D_n$ from the isocenter of the scanner to the center of the nth sub-beam, defined by the nth detector, can be expressed as $(n \pm f)\epsilon$, where n is an integer representing the number of detectors, $f$ represents a positional offset or shift from a nominal dead center position for the detectors and is less than 1 (typically, $f = \frac{1}{4}$ of the detector period, which is the distance between corresponding points on adjacent detectors), and $\epsilon$ is the increment in radial distance from the isocenter to the centers of respective adjacent sub-beams.

Figure 1:
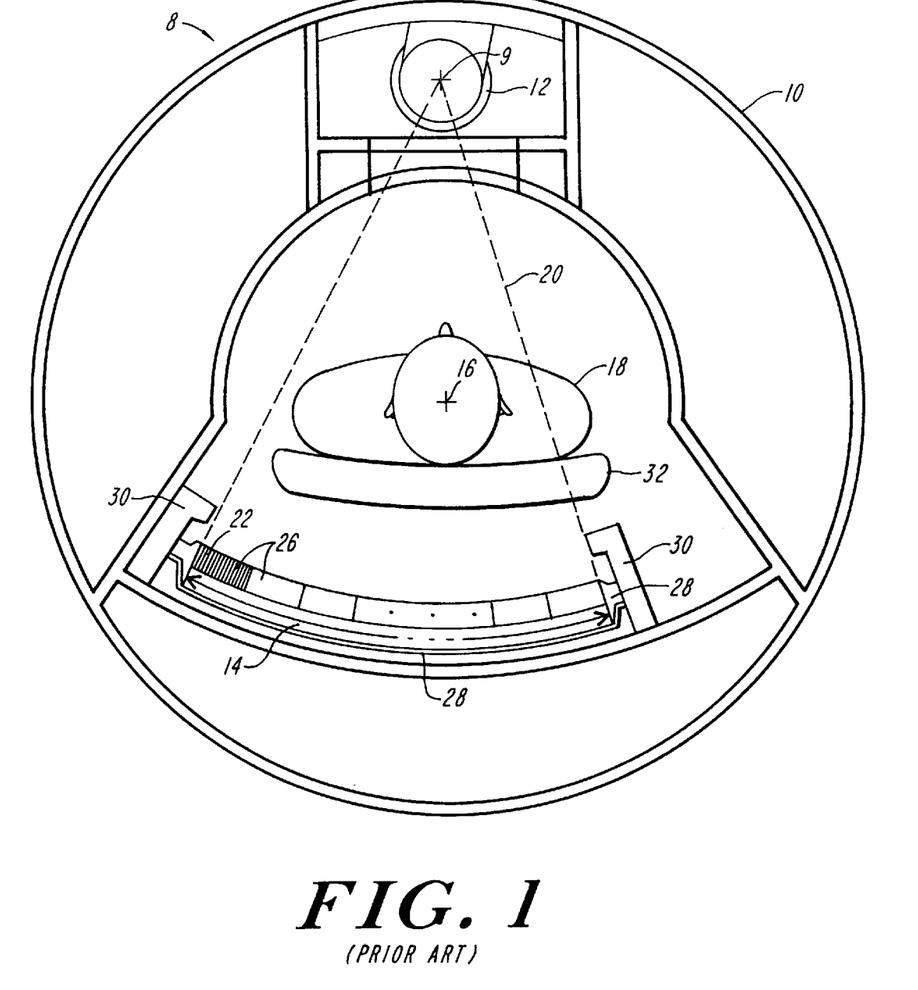
FIG. 1 is an axial view of a CT scanner system as known in the prior art, in which a plurality of arrays of detectors of uniform dimensions is located on a circle centered at the focal spot.

In a typical prior art CT scanner system, illustrated in FIG. 1, a scanner 8 includes a source 12 of X-rays and a detector assembly 14 mounted to a disk 10. To provide the data for a CT scan, source 12 and detector assembly 14 are rotated about a rotation axis 16 (extending normal to the view shown in FIG. 1) so as to rotate around the object 18 that extends through the central opening of the disk during the CT scan. Object 18 may be a part of a live human patient, such as the head or torso. Source 12 emits within the scan plane (normal to rotation axis 16) a continuous fan-shaped beam 20 of X-rays, which emanates from a focal spot 9 and extends to and is sensed by the detectors of assembly 14 after passing through object 18. An array of anti-scatter plates 22 is located between object 18 and the detectors of assembly 14 to substantially reduce the amount of scattered radiation sensed by the detectors.

Disk 10, which may advantageously be of a lightweight material, such as aluminum, is caused to rotate rapidly and smoothly around axis 16. The disk 10 is of an open frame construction so that object 18 can be positioned through the opening of the disk. Object 18 may be supported, for example, on a pallet or table 32, which should be as transparent as practical to x-rays. As disk 10 rotates, detectors of assembly 14 are periodically sampled to provide discrete measurements of x-rays passing in the scanning plane through object 18 from many projection angles. The measurements are then processed electronically with appropriate signal processing equipment (not shown), in accordance with well-known mathematical techniques, so as to produce the final image information. The image information may then be placed in memory, analyzed in a computer, or suitably displayed. In prior art CT scanner systems, such as the system shown in FIG. 1, the detectors (typically between 400 and 1000 in number) are closely spaced along an arc of a circle centered at the focal spot 9 and subtending an angle of typically between 40° and 50°, although both the number of detectors and the angle can vary. The width of each detector is thus on the order of a millimeter. For ease of manufacturing, the detectors in the prior art systems are made to be substantially identical in dimension and are grouped in linear, modular arrays of sixteen or twenty-four detectors which are typically placed approximately along the arc of the circle.

An anti-scatter plate assembly comprising a plurality of anti-scatter plates 22 grouped in modular arrays 26 is also mounted on the support spine 28. The anti-scatter plates 22 are generally aligned with radial lines extending from the focal spot and prevent scattered radiation, i.e., radiation not emanating directly from the x-ray source but instead deflected by dense matter in the patient, from impinging on the detectors.

Figure 2:
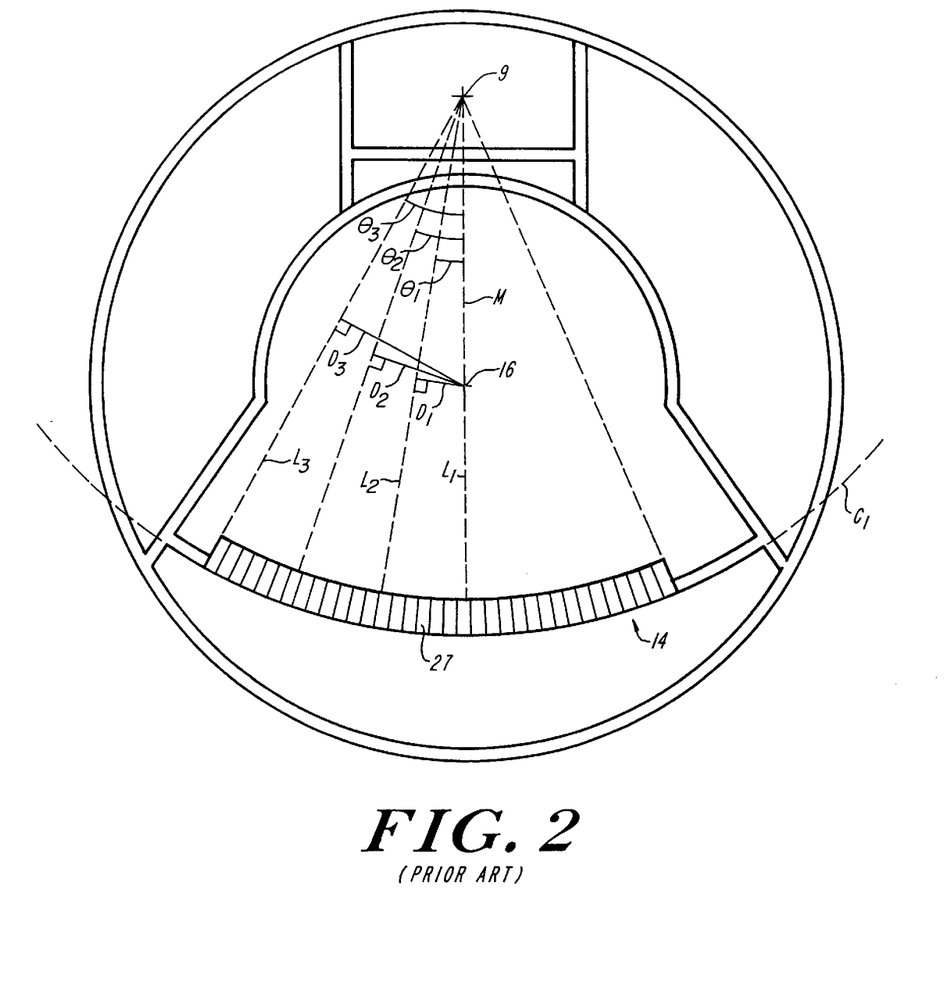
FIG. 2 is a simplified axial view of a prior art CT scanner system, in which the distance from the isocenter to adjacent sub-beams is shown to be a function of the angle between a given sub-beam and a reference ray extending from the focal spot through the isocenter.

As shown in FIG. 2, the detectors 27 in prior art CT scanner systems lie along an arc of a circle $C_1$ centered at the focal spot 9. Each detector 27 defines a unique sub-beam of radiation as that portion of the radiation from the x-ray source which impinges on that detector. The detectors 27 are all of uniform dimension in at least the tangential direction and thus define sub-beams of uniform width in the tangential direction.

In the prior art systems, the distance $D_1, \ldots, D_n$ from the isocenter 16 of the scanner to a given sub-beam $L_1, \ldots, L_n$ is a function of the angle $\theta_1, \ldots, \theta_n$ between the sub-beam of interest and a central ray M which emanates from the focal spot 9 and passes through the isocenter 16. Specifically, the distance $D_n$ is proportional to the sine of the angle $\theta_n$. As a result of this nonlinear relationship, the incremental distance from the isocenter 16 to the centers of respective adjacent sub-beams is not a constant value. As previously mentioned, for scanner systems which use parallel beam image reconstruction algorithms, data from different fan beam projections must be grouped in parallel beam sets and then interpolated to provide sufficient information from which to reconstruct images, and artifacts may be introduced as a result of such interpolation.

Figure 3:
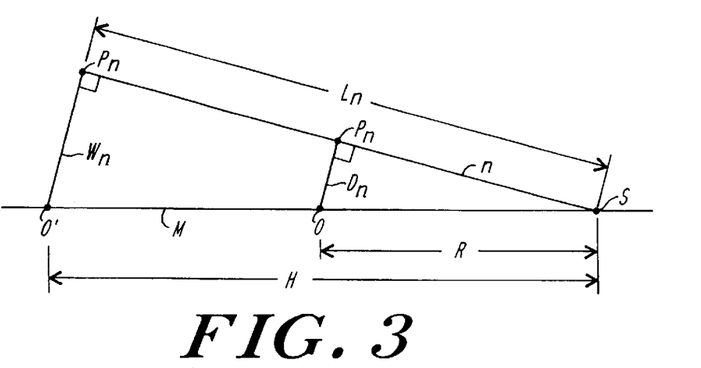
FIG. 3 is a diagram illustrating the geometric relationship of the focal spot, the isocenter, the central ray and the nth sub-beam.

As mentioned previously, in a detector array the distance between adjacent detectors, and thus between adjacent sub-beams of radiation, is defined by the width (i.e., the tangential dimension) of the detectors. However, the distance between adjacent sub-beams that is relevant for image reconstruction is the distance between adjacent sub-beams as measured from the isocenter of the system. As shown in FIG. 3, the distance from the focal spot S to the nth detector is designated as $L_n$. The perpendicular distance from the isocenter O to the nth sub-beam of radiation, which has a length $L_n$, is designated as $D_n$. The distance from the focal spot S to the isocenter O is R, and the distance from the focal spot S to the detector which intercepts the central ray M is H. The distance $D_n$ extends from the isocenter O to point $P_n$ on the nth sub-beam $L_n$, making the triangle $OP_nS$ a right triangle. A second triangle $O'\_P_{n\_}'S$, with point $P_n'$ at the center of the nth detector, is similar to the triangle $OP_nS$ and is thus also a right triangle. The distance $W_n$ from the central ray to the center of the nth detector is proportional to the distance $D_n$ and is equal to $D_nH/R$. It is desired to have the spacing between adjacent sub-beams (i.e., $D_{n+1}-D_n$), as measured from the isocenter of the system, be a constant value, $\epsilon$. This is clearly accomplished by making the value of $W_{n+1}-W_n$ a constant, since the values for H and R are constants.

The angle between any two adjacent sub-beams is very small, as the value of H is typically at least 500 mm and the value of $\epsilon$ is typically 1 mm. The distance $D_n$ is equal to $(n\pm f)\epsilon$, where n is an integer ranging from +1 to the number of detectors in one direction from the central ray M and from −1 to the number of detectors in the opposite direction from the central ray M, $f$ is a number less than 1 which represents the positional offset of the detectors from a nominal dead-center position (typically, $f=\frac{1}{4}$ of the detector period), and $\epsilon$ is the incremental distance from the isocenter O to the centers of respective adjacent sub-beams.

Figure 4:
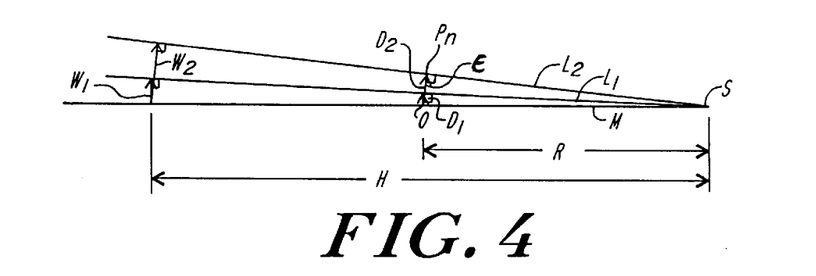
FIG. 4 is a diagram illustrating the geometric relationship of adjacent sub-beams $L_1$ and $L_2$.

As shown in FIG. 4, the distances $D_1$ and $D_2$ are perpendicular to the sub-beams $L_1$ and $L_2$, respectively. The width of any given detector is constant, for ease of manufacturability, and is equal to $(D_2-D_1)H/R$. This relationship will continue to be true if the distance $L_n$ from the focal spot S to the nth detector is adjusted so that the triangle $O'\_P_n'S$ is always a right triangle.

In plane geometry there is a theorem which states that all angles between chords which intersect at the periphery of a circle and which subtend a diameter of the circle are right angles. This is illustrated graphically in FIG. 5, in which OS is a diameter of the circle C. The angles OAS, OA'_S and OA"_S are all right angles.

Figures 5, 6:
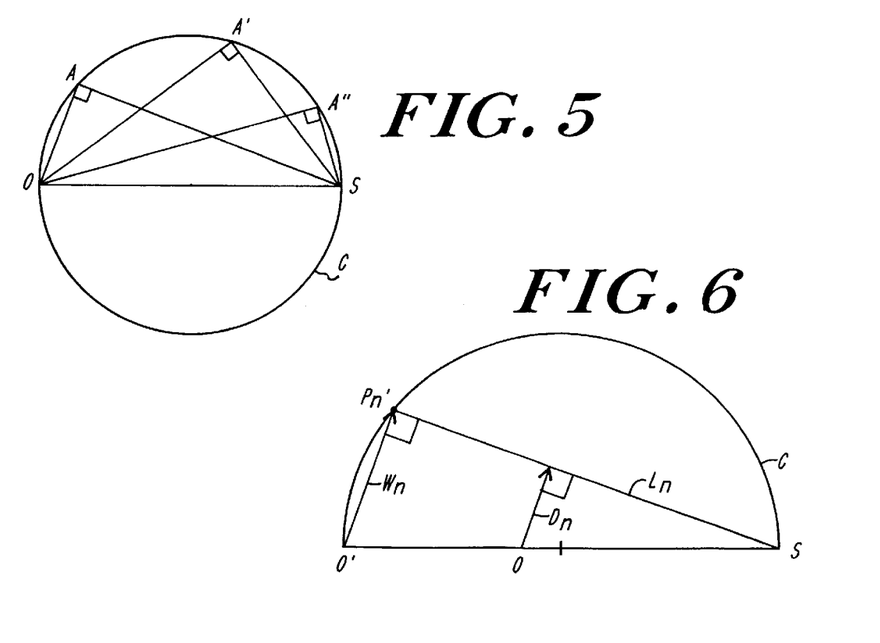
FIG. 5 is a diagram illustrating the geometric theorem relating to right angles subtending a diameter of a circle.
FIG. 6 is a diagram illustrating the geometric relationship between similar right triangles within a detector circle C.

As shown in FIG. 6, by locating each detector on a circle C centered halfway between the focal spot S and O'_, all the triangles $O'\_P_n\_'S$ are right triangles, and the distance $W_n$ from the central ray to the nth detector is always parallel to the perpendicular distance $D_n$ from the isocenter O to the center of the nth sub-beam (i.e., to point $P_n$). Thus, if the distance $W_{n+1}-W_n$ between adjacent detectors is a constant, then the distance between $D_{n+1}-D_n$ will always be a constant value. Note that circle C is not necessarily centered at the isocenter O.

Figure 7:
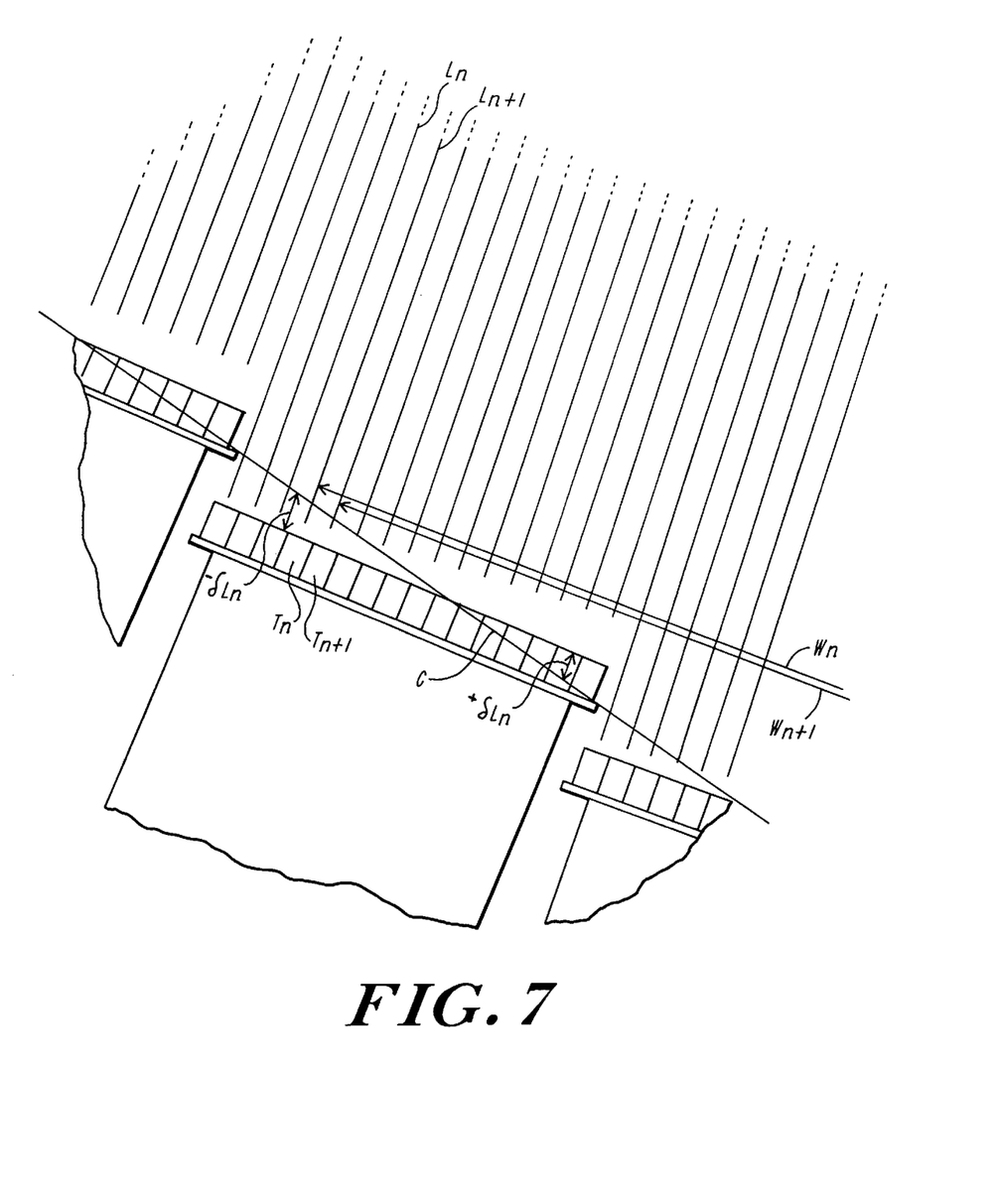
FIG. 7 is a simplified schematic diagram of a portion of a CT scanner system, in which the detector arrays are arranged along the detector circle C so that the cumulative error in the respective distances from the isocenter to adjacent sub-beams is zero.

In practice, the detectors, which are mounted in linear arrays, are only approximately located on the circumference of the circle C, as shown in FIG. 7. Because the sub-beams are almost parallel, the error $\delta L_n$ in the distance $L_n$ from the focal spot S to the nth detector is extremely small (on the order of 2 mm vs. 900 mm) and has only a negligible effect on the distance $D_n$ from the isocenter O to the center of the nth sub-beam. Similarly, the error $\delta D_n$ is extremely small (on the order of 0.1$\epsilon$ or less). Since the errors can be both positive and negative, careful arrangement of the detector arrays on the detector circle C ensures that the actual values for $L_n$ and $D_n$ closely approximate the desired values and also ensures that the cumulative error in the isocenter inter-beam distance $D_n$ is also extremely small relative to $\epsilon$ (on the order of 0.1$\epsilon$ or less). As illustrated in FIG. 7, a detector array can extend both inside and outside the detector circle C, and thus the error can sum to zero over the length of typically one or two detector arrays.

Figure 8:
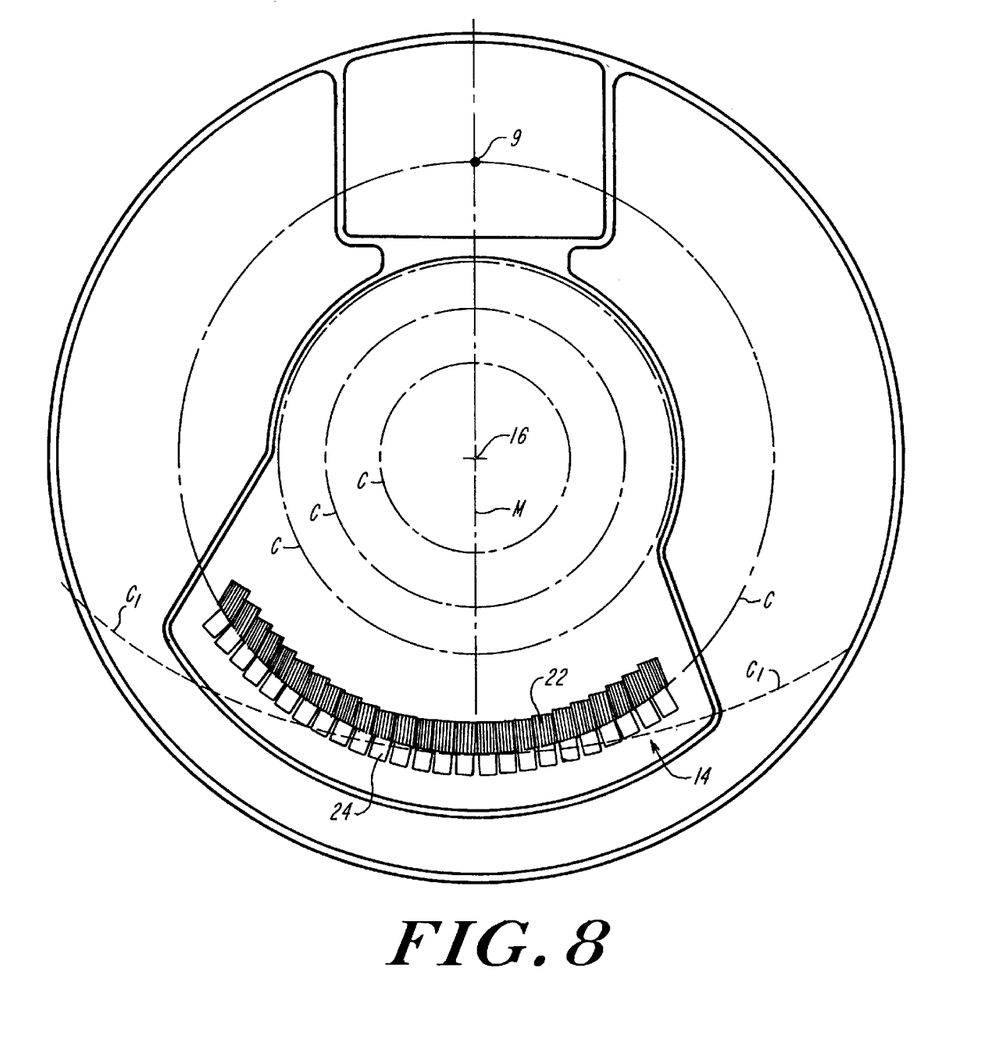
FIG. 8 is an axial view of a CT scanner system according to one embodiment of the invention, in which the detector arrays are located on an arc of a circle C centered at a point which is not coincident with the focal spot.

A CT scanner according to one aspect of the present invention is illustrated in FIG. 8. The detector assembly 14 is located along an arc of a circle C which is not centered at the focal spot 9 but rather at a point on the so-called central ray M extending from the focal spot through the isocenter 16. In a preferred embodiment, the detector circle C is smaller than the circle $C_1$ on which the detectors of prior art systems are located. As a consequence, the radial extent of the detector assembly 14 is less than that of prior art systems, and the detectors are more closely disposed about the object being scanned.

Figure 9:
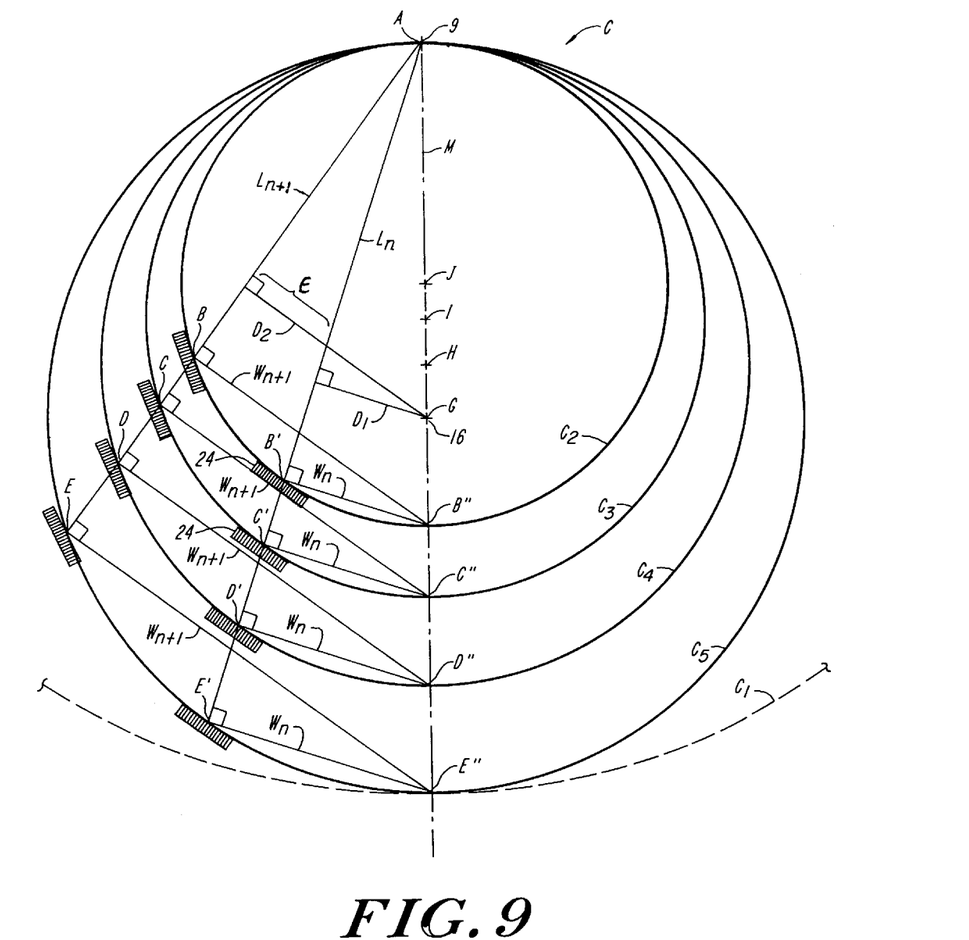
FIG. 9 is a diagram illustrating the family of similar circles C on which the detectors can be placed according to the present invention.

The detector circle C is one of a family of circles which are centered at a point on the ray M passing through both the focal spot 9 and the isocenter 16. In a preferred embodiment, the detector circle has a circumference which passes through the focal spot 9. FIG. 9 illustrates the family of similar circles C on which the detectors can be located in order to ensure that, if the detectors are uniformly spaced from one another so that the value for $W_{n+1}-W_n$ is a constant, the increment in radial distance from the isocenter 16 of the scanner to adjacent sub-beams $L_1$ and $L_2$ (spaced well apart in this diagram for clarity) is a substantially constant value. The prior art detector circle $C_1$, which is centered at the focal spot 9 (point A), is shown in phantom.

A detector can be located at any desired distance from the focal spot. Once that location is selected, the distance H from the focal spot to that detector along the central ray M defines a diameter of the circle on which the detectors will be located.

As shown in FIG. 9, the centers J, I, H and G of each of the respective detector circles $C_2$–$C_5$ according to the invention lie on a central ray M extending from the focal spot 9 (point A) through the isocenter 16 (point G). All angles of chords intersecting the periphery of a given detector circle and subtending a diameter of that circle are right angles, as previously stated. Thus, the right triangles AB'B", AC'C", AD'D" and AE'E" are all similar. The distance between adjacent detectors is thus a constant value and is proportional to the distance between adjacent sub-beams as measured from the isocenter 16 (point G).

It is evident from the diagram of FIG. 9 that the radii of the detector circles $C_2, \ldots, C_n$ can be either larger or smaller than the radius of the prior art detector circle $C_1$. In particular, a smaller detector circle offers several advantages: first, the detectors in this configuration define sub-beams which are substantially uniformly spaced relative to the isocenter of the scanner, making data analysis (at least for parallel beam reconstruction algorithms) simpler and image reconstruction of higher spatial resolution. Second, the detectors in this configuration can be located more closely to the object being scanned, thus requiring less room in the tangential direction and conserving valuable space. Third, the detectors can be made economically as interchangeable modular components with uniform dimensions.

The center of a detector circle C may, but need not, coincide with the isocenter 16 of the scanner, which is located in the range of about 450 to 600 millimeters from the focal spot 9. The detectors are located in the range of about 850 to 1200 millimeters from the focal spot. In a preferred embodiment, the radius of a detector circle C is slightly less than the distance R from the focal spot S to the isocenter O. This placement of detectors relative to the focal spot provides greater flexibility in the utilization of space for other components of the scanner.

Figure 10:
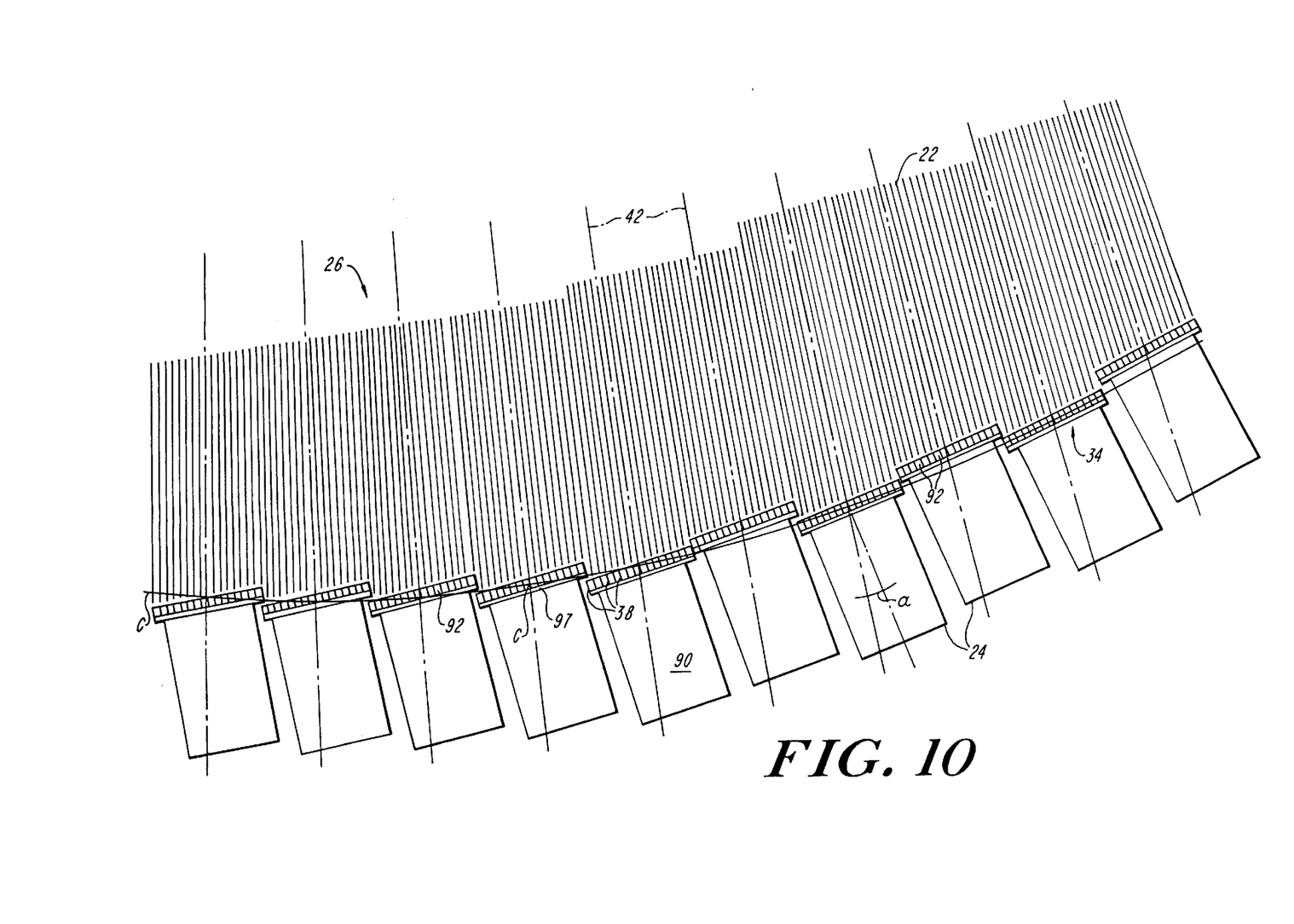
FIG. 10 is a detail view of a portion of the scanner system of FIG. 8.

FIG. 10 is a detail view of a portion of a CT scanner according to a preferred embodiment of the invention, in which a plurality of modular detector arrays 34 are arranged on a detector circle C as previously described. A plurality of anti-scatter plate modules 26 is arranged between the detector modules and the x-ray source (not shown), with the anti-scatter plates 22 aligned substantially with radial lines 42 extending from the focal spot, in order to prevent scattered radiation from impinging on the detectors. The detector arrays 34 are located approximately on the circumference of the detector circle C in an arrangement which ensures that all radiation emanating from the x-ray source impinges on at least a portion of a detector and further ensures that the cumulative error in the inter-beam spacing as measured from the isocenter is zero.

Where feasible, adjacent arrays are staggered in the tangential direction so that the regions of relatively low sensitivity to radiation at the edges of the arrays overlap.

As shown in FIG. 10, a detector module 24 comprises a metal block 90 supporting an array 34 of solid state detector crystals 92. A photodiode 97 underlies the detector array 34. At least a portion of block 90 is preferably narrower than the array 34, to facilitate close placement of the detector arrays without interference of the blocks with one another. The detectors 92 of an array 34 are separated from one another by a layer of highly optically reflective material which reflects visible light photons toward the crystal from which they originate. The reflective material between crystals comprises regions 38 of relatively low sensitivity to radiation. Radiation which impinges on these regions between the crystals is detected at a significantly reduced level, and thus it is desirable to avoid or minimize impingement of radiation directly on this area. In a preferred embodiment, these regions of low sensitivity to radiation between detector crystals 92 are not aligned with radial lines 42 extending from the focal spot (not shown), so that radiation from the x-ray source impinges on at least a portion of at least one detector crystal and not only on the regions between the crystals. This is accomplished by tilting the detector modules 24 at an angle α with respect to radial lines 42. In a preferred embodiment, the respective detector modules 24 and the arrays 34 mounted thereon are tilted at an angle α of either +9° or -9° from a nominally perpendicular orientation relative to radial lines 42. Note also that the ends of adjacent arrays 34 are overlapped, or staggered, in the tangential direction. This arrangement of the detector arrays optimizes their placement along the detector circle C and eliminates the need for additional space in the tangential direction to accommodate as-manufactured variations in the dimensions of the arrays. In addition, as previously mentioned, with this array configuration the cumulative error in the inter-beam spacing as measured from the isocenter sums to zero over one or two array lengths.

As can also be seen in FIG. 10, the anti-scatter plates 22 are generally aligned with the radial lines 42 extending from the focal spot to prevent scattered radiation from reaching the detector crystals. In a preferred embodiment, the anti-scatter plates 22 are substantially aligned with regions of constant maximum sensitivity of corresponding detectors, and not with the regions of relatively low sensitivity to radiation between the detector crystals. Although the number of anti-scatter plates in this embodiment is equal to the number of detectors, it need not be and can be either greater or fewer than the number of detectors.

Figure 11:
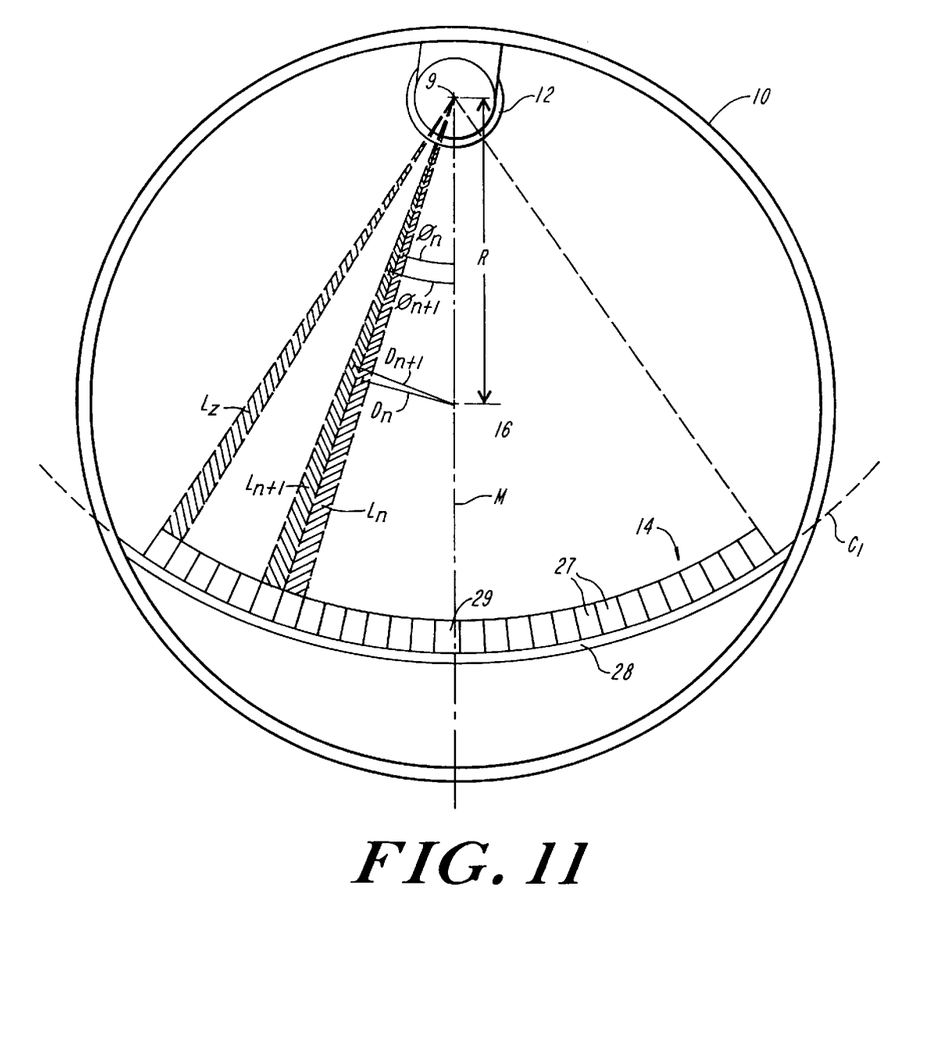
FIG. 11 is an axial view of a CT scanner system according to another embodiment of the invention, in which detectors of non-uniform widths are located on a circle $C_1$ centered at the focal spot.
Figure 12:
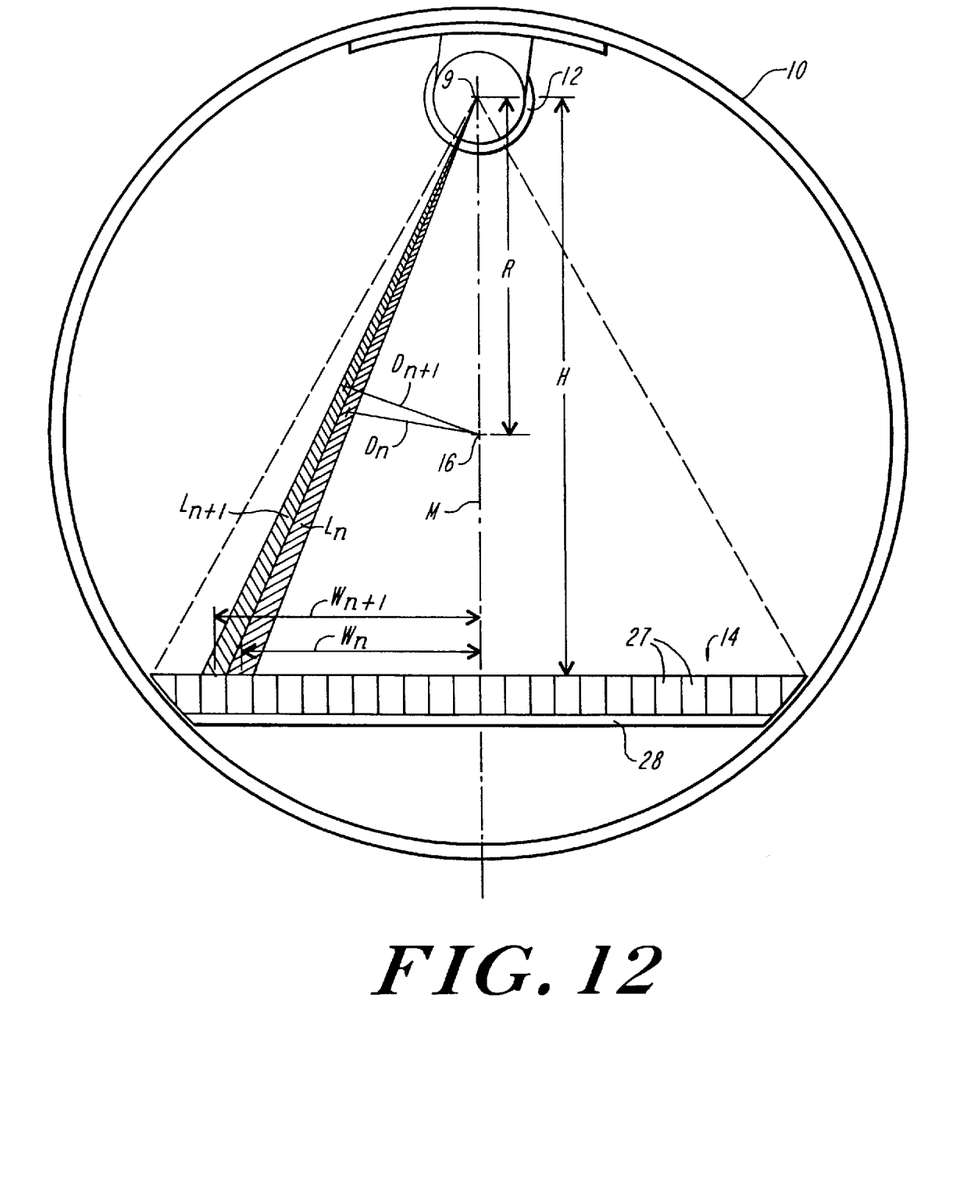
FIG. 12 is an axial view of a CT scanner system according to still another embodiment of the invention, in which detectors of non-uniform widths are located on a substantially straight line at a preselected distance from the focal spot.

CT scanners according to alternate embodiments of the invention are shown in FIGS. 11–12. As shown in FIG. 11, it is possible to achieve the objective of substantially uniform sub-beam spacing as measured from the isocenter of the scanner by locating detectors of non-uniform widths at a uniform distance from the focal spot 9, such as along a circle $C_1$ centered at the focal spot 9. In this embodiment, the detector assembly 14 comprises a plurality of discrete detectors 27 having widths that vary by as much as approximately 15%. The detectors 27 define sub-beams $L_n$, $L_{n+1}$ of different widths, the narrowest detectors being located closest to the central ray M, and the widest detectors being located farthest from the central detector 29 and defining the widest sub-beam $L_z$. It should be noted that although the variation in detector width is as much as about 15%, the differences in the detector widths are greatly exaggerated in this diagram for clarity.

In general, the distance from the focal spot 9 to the isocenter is designated as R, and the nth sub-beam $L_n$ is located at an angle $\phi_n$ from the central ray M. Accordingly, the distance $D_n$ from the isocenter 16 to the center of the nth sub-beam $L_n$ is expressed as:

$$D_n = R \sin \phi_n, \quad (1)$$

and $$\phi_n = \arcsin (D_n/R). \quad (2)$$

To ensure that the incremental distance ε from the isocenter 16 to the centers of respective adjacent sub-beams $L_n$, $L_{n+1}$ is a constant value, we define the distance from the isocenter to the center of a given sub-beam $L_n$ to be a constant value, expressed as:

$$D_n = |n+f|\epsilon, \quad (3)$$

and $$\phi_n = \arcsin \{|n+f|\epsilon/R\}, \quad (4)$$

wherein n is an integer ranging from +1 to the number of detectors in one direction from the central ray M and from −1 to the number of detectors in the opposite direction from the central ray M, $f$ is a number less than 1 which represents the positional offset of the detectors from a nominal dead-center position (typically, $f=¼$ of the detector period), and $\epsilon$ is the incremental distance from the isocenter 16 to the centers of respective adjacent sub-beams $L_n$, $L_{n+1}$.

Alternatively, as shown in FIG. 12, detectors 27 of varying widths in the tangential direction can be located other than equidistant from the focal spot, such as on a substantially straight line which is at a preselected distance from the focal spot, or on circles not centered at the focal spot, or other loci as well.

In the embodiment of FIG. 12, the detectors 27 have varying widths and define sub-beams $L_n$, $L_{n+1}$ of different widths, the narrowest detectors being located closest to the central ray M and the widest detectors being located farthest from the central ray M. Adjacent sub-beams $L_n$, $L_{n+1}$ are shown adjacent in this diagram. The variation in detector width, as much as about 15%, is again exaggerated in this diagram for clarity.

The increment in radial distance $\epsilon$ from the isocenter 16 to the centers of adjacent sub-beams $L_n$ and $L_{n+1}$ is a substantially constant value if the distance $W_n$ is defined as the distance from the central ray M to the center of a given sub-beam $L_n$, R is the distance from the focal spot 9 to the isocenter 16, and H is the distance from the focal spot to the detector 29 which is located on central ray M. Accordingly, $$W_n = D_n H/(R^2 - D_n^2)^{1/2},$$

and $$D_n = |n+f|\epsilon, \quad (6)$$

wherein, as above, n is an integer ranging from +1 to the number of detectors in one direction from the central ray M and from −1 to the number of detectors in the opposite direction from the central ray M, $f$ is a number less than 1 which represents the positional offset of the detectors from a nominal dead-center position, and $\epsilon$ is the incremental distance from the isocenter 16 to the centers of respective adjacent sub-beams $L_n$ and $L_{n+1}$.

Other loci for the detectors which optimize geometric efficiencies and/or tolerate the use of variable-width detectors are not shown but are considered to be within the scope of the present invention.

Because certain changes may be made in the above apparatus without departing from the scope of the invention herein disclosed, it is intended that all matter contained in the above description or shown in the accompanying drawings shall be interpreted in an illustrative and not a limiting sense.

We claim:

1. An x-ray scanning system comprising:
   an x-ray source for defining a focal spot from which a beam of radiation is emitted;
   an x-ray detector assembly including a plurality of x-ray detectors arranged in an array and cooperative with said x-ray source so as to define the beam of radiation from the focal spot to all of the detectors;
   means for supporting the x-ray source and the detector assembly for rotation in a rotation plane about a rotation axis so as to define an isocenter, wherein said radiation beam includes a plurality of sub-beams, each sub-beam being defined as that portion of the radiation beam impinging on a single detector; and
   means for configuring the detectors so that the increment in radial distance from the isocenter to the centers of any two adjacent sub-beams is a substantially constant value.

2. The x-ray scanning system of claim 1, wherein said means for configuring the detectors comprises means for locating the detectors substantially on a circle centered at a point other than the focal spot.

3. The x-ray scanning system of claim 2, wherein said detectors are grouped in substantially linear arrays and wherein the centers of said arrays are located approximately on an arc of said circle within the plane of rotation of the x-ray source, said circle being selected from the family of circles having a circumference which passes through the focal spot and being centered at a point on a line which extends from the focal spot and passes through the isocenter.

4. The x-ray scanning system of claim 3, further including an anti-scatter plate assembly mounted on said supporting means, said anti-scatter plate assembly including a plurality of anti-scatter plates disposed between the x-ray source and said detector assembly, and means for mounting said anti-scatter plate assembly relative to said detector assembly so that said anti-scatter plates are substantially aligned with radial lines extending from the focal spot, wherein the radiation detected by the detector assembly is substantially limited to radiation emitted directly from the x-ray source.

5. The x-ray scanning system of claim 4, wherein said anti-scatter plates are substantially aligned with regions of substantially constant maximum sensitivity of corresponding detectors.

6. The x-ray scanning system of claim 5, wherein the number of anti-scatter plates is equal to the number of detectors.

7. The x-ray scanning system of claim 5, wherein the number of anti-scatter plates is not equal to the number of detectors.

8. The x-ray scanning system of claim 5, wherein the increment in radial distance from the isocenter to proximate sub-beams defined by corresponding proximate detectors in adjacent arrays is approximately equal to the increment in radial distance from the isocenter to adjacent sub-beams defined by corresponding adjacent detectors in a single array.

9. The x-ray scanning system of claim 8, wherein adjacent detectors in an array are spaced apart from one another by a region of relatively low sensitivity to radiation, and wherein the detector arrays are oriented at a preselected angle $\alpha$ with respect to a nominally perpendicular orientation of said arrays relative to radial lines extending from the focal spot to approximately the centers of said arrays, wherein the regions of relatively low sensitivity to radiation between adjacent detectors in an array are not aligned with said radial lines.

10. The x-ray scanning system of claim 9, wherein each of said detectors includes a detector crystal for sensing said radiation, and wherein the absolute value of said angle $\alpha$ is a function of the height of the detector crystal and the width of the regions of relatively low sensitivity to radiation between adjacent crystals in an array.

11. The x-ray scanning system of claim 10, wherein the angle $\alpha$ includes both positive and negative values for said angle.

12. The x-ray scanning system of claim 1, wherein said means for configuring the detectors comprises means for defining a plurality of sub-beams which subtend a plurality of different angles.

13. The x-ray scanning system of claim 12, wherein the means for defining a plurality of sub-beams which subtend a plurality of different angles comprises a plurality of detectors having a corresponding plurality of different widths in the tangential direction, and means for defining a locus of said detectors with respect to said focal spot, wherein the width in the tangential direction of a given detector is a function of the location of said given detector with respect to a central ray extending from the focal spot and passing through the isocenter.

14. The x-ray scanning system of claim 13, wherein the locus of said detectors is a circle centered at the focal spot.

15. The x-ray scanning system of claim 13, wherein the locus of said detectors is a substantially straight line at a preselected distance from the focal spot.

* * * * *